(12) United States Patent
Oevering et al.

(10) Patent No.: US 7,371,884 B2
(45) Date of Patent: May 13, 2008

(54) PROCESS FOR PREPARING SUCCINONITRILE AND USE OF SUCCINONITRILE

(75) Inventors: Hendrik Oevering, Elsloo (NL); Franciscus H. A. M. Vandenbooren, Maastricht (NL); Olaf Poorter, Maastricht (NL)

(73) Assignee: DSM IP Assets B.V., Heerlen (NL)

(*) Notice: Subject to any disclaimer, the term of this patent is extended or adjusted under 35 U.S.C. 154(b) by 157 days.

(21) Appl. No.: 10/497,781

(22) PCT Filed: Dec. 3, 2002

(86) PCT No.: PCT/NL02/00782

§ 371 (c)(1),
(2), (4) Date: Jun. 6, 2006

(87) PCT Pub. No.: WO03/050079

PCT Pub. Date: Jun. 19, 2003

(65) Prior Publication Data

US 2006/0229463 A1    Oct. 12, 2006

(30) Foreign Application Priority Data

Dec. 11, 2001 (EP) .................................. 01204866

(51) Int. Cl.
*C07C 253/10* (2006.01)

(52) U.S. Cl. ....................................... 558/332

(58) Field of Classification Search ............... 558/332
See application file for complete search history.

(56) References Cited

U.S. PATENT DOCUMENTS

| 2,434,606 A | 1/1948 | Carpenter |
| 5,254,738 A | 10/1993 | Koehler |

FOREIGN PATENT DOCUMENTS

| DE | 2719867 | 11/1978 |

OTHER PUBLICATIONS

Derwent Publications, AN 1975-35215W, English Abstract of JP 50 010848, Apr. 24, 1975.

*Primary Examiner*—Kamal A. Saeed
(74) *Attorney, Agent, or Firm*—Nixon & Vanderhye P.C.

(57) ABSTRACT

The invention relates to a process for preparing succinonitrile by contacting acrylonitrile (ACN) with hydrocyanic acid (HCN) in a reactor in the presence of a tertiary amine. The invention also relates to the use of succinonitrile prepared according to the process of the invention, for preparing diaminobutane. Succinonitrile is prepared by contacting ACN with HCN in the presence of a tertiary amine and a compound chosen from the group consisting of water, aliphatic alcohols, aromatic alcohols, carboxylic acids and mixtures thereof.

16 Claims, No Drawings

PROCESS FOR PREPARING SUCCINONITRILE AND USE OF SUCCINONITRILE

CROSS REFERENCE TO RELATED APPLICATION

This application is the National Phase of International Application PCT/NL02/00782, filed Dec. 3, 2002, which was published in the English language.

The invention relates to a process for preparing succinonitrile (SN) by contacting acrylonitrile (ACN) with hydrocyanic acid (HCN) as reactants in a reactor in the presence of a tertiary amine. The invention also relates to the use of succinonitrile (SN) prepared according to the process of the invention, for preparing diaminobutane (DAB).

A process for the preparation of SN is known from DE-A-2,719,867, according to which the reaction of HCN with ACN is carried out in a reactor in the presence of a tertiary amine, for which a wide variety of tertiary amines can be used. A disadvantage of the known process is that tricyanobutane (TCB) is formed as a by-product. SN is known as a raw material for preparing 1,4-diaminobutane via hydrogenation. TCB disturbs the hydrogenation process by poisoning of the hydrogenation catalyst. Therefore, prior to the hydrogenation, SN has to be purified, e.g. by a distillation process. In such a distillation process SN cannot be distilled off quantitatively to yield a residue rich in TCB, because of the risk of exothermic polymerization of TCB. Therefore, such a purification process always results in a substantial loss of SN.

The object of the present invention is to provide a process for preparing SN that results in a lower amount of TCB relative to SN.

This object is achieved in that the process is carried out in the presence of a compound chosen from the group consisting of water, aliphatic alcohols, aromatic alcohols, carboxylic acids and mixtures thereof.

The effect of the presence of a compound chosen from the group consisting of water, aliphatic alcohols, aromatic alcohols, carboxylic acids and mixtures thereof is that the amount of TCB formed as a by-product, relative to SN, is reduced. A further advantage of the process according to the invention is a higher yield in purified SN.

U.S. Pat. No. 2,434,606, discloses a process for preparing SN from ACN and HCN, which process is carried out in the presence of an alkaline catalyst. The alkaline catalyst may be alkali metal hydroxides, earth alkali metal hydroxides, alkali metal cyanides, alkali metal carbonates, or other alkali metal salts of weak acids as well as organic bases. Examples are given in which potassium cyanide, calcium hydroxide and benzylammonium hydroxide are used as the catalyst and the process is carried out in the presence of water. However, one of the claimed processes in U.S. Pat. No. 2,434,606 comprises reacting ACN with HCN in the presence of basic inorganic cyanide under anhydrous conditions and at a temperature of 30° C. to 55° C. In other examples, the process is carried out in the presence of aliphatic amines, without mentioning the presence of any water, aliphatic alcohol, aromatic alcohol or carboxylic acid. The problem of formation of TCB as related to the process carried out in the presence of tertiary amines is not mentioned, neither is there any indication that the formation of TCB, relative to SN, can be reduced by carrying out the process according to the invention in the presence of water, an aliphatic alcohol, an aromatic alcohol, a carboxylic acid or mixtures thereof.

According to DE-B-1,007,313, use of the catalysts mentioned in above cited U.S. Pat. No. 2,434,606 involves a number of disadvantages, such as, for instance, insufficient purity of the resulting product. Accordingly, in DE-B-1,007,313, other catalysts, i.e. tertiary alkali metal phosphates and alkali metal pyrophosphates, have been proposed for the preparation of SN from the reaction of ACN with HCN. The alkaliphosphates can be used in water-free form or with crystal water. According to DE-B-1,007,313, the process is preferably carried out with water-free ACN and HCN, though small amounts of water, e.g. 1 to 5%, can be used without special disadvantage. However, larger amounts should be avoided, since this leads to lower yields. There is no indication in DE-B-1,007,313 of the problem underlying the present invention, neither for the solution according to the present invention.

The process of the invention can be carried out in a reactor, to which ACN, HCN, the compound chosen from the group of water, aliphatic alcohols, aromatic alcohols, carboxylic acids and mixtures thereof, the tertiary amine and optionally other compounds, for instance a non-reactive diluent, are added, thereby forming a reaction mixture comprising ACN, HCN and/or reaction products thereof, the compound chosen from the group of water, aliphatic alcohols, aromatic alcohols, carboxylic acids and mixtures thereof, the tertiary amine and optionally other compounds present in said mixture. The process of the invention can be carried out in any reactor suitable for the reaction of ACN with HCN. Examples of suitable reactors are, for instance, a stirred batch reactor, a continuous stirred tank reactor, or a loop reactor. Also any process set-up, suitable for the process of preparing succinonitrile by contacting ACN with HCN, can be chosen for carrying out the process of the invention. Suitable process set-ups are, for instance, a batch process, a continuous process, a cascade process, or a loop process.

For carrying out the process of the invention, ACN, HCN, the compound chosen from the group consisting of water, aliphatic alcohols, aromatic alcohols, carboxylic acids and mixtures thereof, the tertiary amine and optionally other compounds, may be added in different orders. In, for instance, a batch process the compound may be supplied in advance of the addition of either ACN or HCN or both. The compound may also be added parallel to or together with either one of the two reactants. The compound can be added or made-up from a separate source or via any of the supplies of the tertiary amine, HCN and ACN, and the compound might as well be supplied from an internal recycle stream. In case the compound is a carboxylic acid, the compound might also be supplied in the form of a salt of the carboxylic acid and a tertlairy amine.

The order of the addition of ACN, HCN and the tertiary amine is not critical to obtain the desired result of the process. For example, HCN is added to and mixed with a reactor content comprising the compound chosen from the group of water, aliphatic alcohols, aromatic alcohols, carboxylic acids and mixtures thereof, the tertiary amine and optionally other compounds, for instance a non-reactive diluent, and after that ACN is added to and mixed with the reactor content. Alternatively, but not limited thereto, after HCN and ACN are added, the tertiary amine is added to the reactor.

In the process of the invention, a reaction between ACN and HCN takes place. Upon completion of the reaction, the resulting reaction mixture can be separated by, for instance, fractionated distillation at reduced pressure, into different fractions comprising, as a major component, SN, respectively the compound chosen from the group of water, aliphatic alcohols, aromatic alcohols, carboxylic acids and mixtures thereof, the tertiary amine and/or any excess of ACN or HCN, if still present. The compound, the tertiary amine and/or any excess of ACN or HCN, if still present, thus separated, can be reused in the process as described.

In the reaction mixture contained in the reactor, the concentrations of ACN and HCN may change over time and/or in place. For instance if the process according to the invention is carried out as a batch process the concentrations will change over time, due to consumption of ACN and HCN, together called the reactants. In for instance a well-balanced continuous process, ACN, HCN, the tertiary amine and the compound are preferably added in such a way that a steady state is formed. In the latter process, the concentrations will vary in place, but will be substantially invariable over time.

When a (maximum) concentration of a component being any of the reactants, the compound, the tertiary amine or non-reactive diluent present in the reaction mixture, is discussed further below in this application, this concentration is meant in a batch process to relate to the average concentration of said component in the reaction mixture at any specific moment during the process, and in a continuous process to relate to the average concentration of this component in the reactor.

In the process according to the invention, the compound chosen from the group consisting of water, aliphatic alcohols, aromatic alcohols, carboxylic acids and mixtures thereof, may be present in an amount, which may be varied widely. Preferably, the compound is present in an amount of at least 1% by weight, calculated relative to the reactants. The weight of the reactants is equal to the amounts of ACN and HCN supplied to the reactor for a batch process or to the average amounts present in the reactor for a continuous process. Improved results in terms of reduced TCB formation are obtained when the compound is present in an amount of at least 3% by weight, calculated relative to the reactants. Still more preferably, the compound is present in an amount of at least 10% by weight, calculated relative to the weight of the reactants. This embodiment of the invention has the advantage that the amount of TCB formed, relative to SN, is further reduced. Even more preferable, the compound is present in an amount of at least 25% by weight, calculated relative to the reactants. With such high amounts of the compound, TCB formation is extremely low if not absent at all. The amount of the compound can be much higher, for instance above 50% by weight, calculated relative to the reactants. Preferably, the amount is below 50%. This allows a better reactor capacity utilization.

The maximum amount of the compound in the reaction mixture in the reactor is in principle only limited for practical reasons, such as optimization of utilization of reactor volume. For that reason, the amount of the compound preferably is at most 25% by weight, calculated relative to the total of ACN, HCN and/or reaction products thereof, the compound chosen from the group of water, aliphatic alcohols, aromatic alcohols, carboxylic acids and mixtures thereof, the tertiary amine and any non-reactive diluent present in the reactor. More preferably the amount of the compound is at most 15% by weight, calculated relative to said total. This embodiment of the invention has the advantage that the relative amount of the compound, that has to be separated from the reaction mixture after the process has been carried out, is limited.

In the process according to the invention, as the compound chosen from the group consisting of water, aliphatic alcohols, aromatic alcohols; carboxylic acids and mixtures thereof, preferably the compound is chosen from the group consisting of water, aliphatic alcohols and mixtures thereof. More preferably at least water is present. Water has a strong reducing effect on the relative amount of TCB formed relative to SN, which effect can already be observed when water is present in a very low amount. More preferably, the compound consists of water, since water gives the best results and this makes purification of SN easier.

The compound may also comprise at least an aliphatic alcohol. Preferably the aliphatic alcohol is chosen from the group of C1-C12 alcohols. The aliphatic alcohol may be linear or branched, and may be a primary, a secondary as well as a tertiary alcohol. Suitable aliphatic alcohols are for instance methanol, ethanol, propanol, isopropanol, butanol, isobutanol, and 2-ethylhexylalcohol. Lower boiling, short chain aliphatic alcohols are more preferred, because these are more effective per unit weight and have the advantage that they can more easily be separated from SN by distillation.

The compound may also comprise at least an aromatic alcohol. Preferably the aromatic alcohol is phenol or a substituted phenol, most preferably phenol. Use of phenol as the compound results in a lower amount of TCB formed relative to SN, and in an increase in conversion rate of ACN and HCN into SN.

The compound may also comprise at least a carboxylic acid. The advantage is that a lower amount of TCB relative to SN is formed and the conversion rate of ACN and HCN into SN is increased. More preferably, the carboxylic acid is a carboxylic acid with a short alkyl chain, in particular chosen from the group of acetic acid, propionic acid, butyric acid and iso-butyric acid. Most preferably the carboxylic acid is acetic acid. The advantage is a higher efficiency per unit weight of the carboxylic acid compound.

The process of the invention is carried out in the presence of a tertiary amine. As tertiary amine a large variety of compounds can be used, such as heterocyclic tertiary amines, bicyclic tertiary amines and in particular amines of the chemical formula (I):

(I)

in which $R^1$, $R^2$ and $R^3$ independently of each other can be an alkyl-, cycloalkyl-, aralkyl- or aryl-group. Suitable tertiary amines are known from the art, such as those mentioned in DE-A-2,719,867. Preferably, the tertiary amine is a trialkyl amine. Particular suitable trialkyl amines are low boiling trialkyl amines, such as trialkyl amines of formula (I) in which $R_1$, $R_2$ and $R_3$ are C1-C4 alkyl groups, such as methyl-, ethyl-, propyl-, i-propyl, n-butyl, sec-butyl, i-butyl and tert-butyl groups, and low boiling bicylic tertiary amines, such as triethylene diamine. More preferably, the low boiling trialkyl amine is trimethylamine, ethyldimethylamine, propyldimethylamine, butyldimethylamine, pentyldimethylamine, triethylamine, diethylpropylamine, diethylbutylamine, diethylpentylamine, and tripropylamine.

Preferably the tertiary amine is used in a concentration of at least 2% by weight, calculated relative to the total of ACN, HCN and/or reaction products thereof, the compound chosen from the group consisting of water, aliphatic alcohols, aromatic alcohols, carboxylic acids and mixtures thereof, the tertiary amine and any non-reactive diluent present in the reactor. This has the advantage that the rate for the conversion of ACN with HCN is increased. The concentration of tertiary amine in excess of the indicated amount of 2% by weight may be varied within certain limits. A concentration up to or over, for instance, 20% by weight of said total, if desired, can be used. For practical purposes a concentration of from 3 to 15% by weight, calculated relative to said total, is very suitable. This has the advantage that the reaction rate is further increased at limited costs.

Most preferably, the tertiary amine is triethylamine. The advantage of triethylamine is that it has a boiling point, which is lower than that of SN, by which it can easily be separated from SN by fractionated distillation.

The amount of ACN relative to HCN can be varied. Preferably, ACN is used in excess over HCN to assure that all HCN will be converted. It has been found advantageous to keep the excess of ACN over HCN limited. If the process is carried out as a batch process, preferably ACN and HCN are contacted in a mole ratio of ACN:HCN of at least 1.00:1 up to at most 1.25:1. This has the advantage, compared to a larger excess, that the amount of TCB formed, relative to the amount of SN formed, is reduced. More preferably, ACN and HCN are contacted in a mole ratio of ACN:HCN of at least 1,00:1 up to at most 1.10:1. This has the advantage that the TCB formation, if any, is even further reduced. In a continuous process, ACN is preferably present in a concentration in excess over HCN. For practical reasons, such as utilization of reactor volume, the concentration of ACN in excess over HCN is at least 1%. More preferably, the concentration of ACN in the reaction mixture in excess over HCN is at least 3%.

It has been found advantageous to keep the maximum concentration of ACN in the reaction mixture in the reactor low. A low concentration results in formation of a lower amount of TCB, relative to the amount of SN formed, in comparison to a process conducted with a higher ACN concentration. Preferably, ACN is present in a concentration of at most 35% by weight, calculated relative to the to the total of ACN, HCN and/or reaction products thereof, the compound chosen from the group consisting of water, aliphatic alcohols, aromatic alcohols, carboxylic acids and mixtures thereof, the tertiary amine and any non-reactive diluent present in the reactor. More preferably, the maximum ACN concentration is below 20%, by weight, calculated relative to said total, since this results in even lower amounts of TCB.

A way to control the ACN concentration is to carry out the process in a non-reactive diluent. A non-reactive diluent is meant to be a liquid that is inert in respect to ACN, HCN, the tertiary amine and the compound chosen from the group consisting of water, aliphatic alcohols, aromatic alcohols, carboxylic acids and mixtures thereof, and can act as a solvent or diluent for these. The advantage of carrying out the process in such a way that the reaction mixture comprises a non-reactive diluent, is that the concentration of ACN can be kept low and that TCB is formed in lower amounts, relative to the amount of SN formed. Suitable reactive diluents are, for example, hexane, toluene and SN. Preferably, the non-reactive diluent is SN. More preferably, SN is present in an amount of at least 40% by weight, calculated relative to the total of ACN, HCN and/or reaction products thereof, the compound chosen from the group consisting of water, aliphatic alcohols, aromatic alcohols, carboxylic acids and mixtures thereof, the tertiary amine and succinonitrile present in the reactor. SN can even be present in very high amounts; because of reasons of process efficiency the amount is for example not more than 95% by weight, calculated relative to said total.

The process is advantageously carried out at temperatures in the range of about 50° C. to about 110° C., preferably 60° C. to 80° C., and usually at atmospheric pressure, though other pressures can be used as well. The temperature may be controlled if necessary by external heating and cooling.

Succinonitrile (SN) is a useful product known as a raw material for preparing e.g. 1,4-diaminobutane, which can, for instance, be used for the preparation of polyamide-4,6.

In a process for preparing diaminobutane from SN, SN is hydrogenated in the presence of a hydrogenation catalyst. The problem of such a process is that TCB disturbs the hydrogenation by poisoning of the hydrogenation catalyst. This problem is at least reduced or is completely solved by using SN prepared according to the process of the invention. Therefore, the invention also relates to a process for preparing diaminobutane using SN prepared according to the process of the invention.

The invention relates in particular to a process for preparing 1,4-diaminobutane (DAB) comprising the steps of a) contacting acrylonitrile (ACN) with hydrocyanic acid (HCN) in the presence of a tertiary amine, b) isolating succinonitrile (SN) from the reaction mixture of step a), c) hydrogenating said SN of step b) with a suitable hydrogenation catalyst, d) isolating DAB from the reaction mixture of step c). This process has the advantage that in step a) less TCB, relative to SN, is formed, that in step b) the loss of SN can be reduced and in step c) the risk of poisoning the hydrogenation catalyst by TCB can be better kept under control. Such a process is particularly advantageously carried out, when as the compound water is used. As the tertiary amine, preferably triethylamine is used.

The invention is further elucidated with the following, non-limiting, examples.

Methods

Gaschromatography

For the determination of the TCB content in the reaction mixtures a Hewlett Packard Gaschromatograph, type HP 5890, series II, equipped with a column HP-5, length 25 m, internal diameter 0.32 mm, material fused silica, stationary phase HP-5, film thickness 1.05 µm, was used. A temperature program was set, with start temperature 80° C., ramp 10° C./min, end temperature 250° C. The carrier gas was helium, with average linear gas speed 25 cm/s. A sample was prepared of about 0.1-4% in a water/pyridine mixture (volume ratio 1:1). 10 µl sample was put in the autosampler; 1.0 µl was injected with a split type injection with a split 1:100 at an injection temperature of 250° C. For the analysis a flame ionization detector was used at a temperature of 300° C. and range 3. The peaks of the resulting chromatogram were integrated with a Packard LDS-datasystem to determine the peak surface areas. The concentration of the components was determined on the basis of the peak surface areas with the help of internal standards.

Titration of HCN

For determination of the HCN content in the reaction mixtures, 1 gram sample of the reaction mixture was dissolved in about 10 ml 1 N NaOH and stirred for 1 hour at room temperature. After addition of about 75 ml water the solution was titrated with 0.01 Mol/L silvemitrate (AgNO$_3$). The equilibrium point was determined with an ion specific Ag/Ag$_2$S electrode against a double junction reference electrode.

EXAMPLE 1

A 150 ml double glass reactor, fitted with a turbine stirrer and baffles and equipped with a reflux cooler, was charged with 50 grams succinonitrile, 0.5 gram water and 10 grams triethylamine. The temperature of the reflux cooler was kept at −9° C. while the reactor content was heated to 70° C. Then 20.0 grams ACN and 9.3 grams HCN were dosed simultaneously in 30 seconds. The reaction was followed by determining titrimetrically the HCN content until HCN was converted completely. Then the TCB content in the reaction mixture was determined with gaschromatography, as a percentage of the total reaction mixture. The resulting TCB content is reported in Table I.

EXAMPLE 2

Example 2 was executed as example 1, except that 1.0 gram water, in stead of 0.5 gram water, was charged to the reactor. The resulting TCB content is reported in Table I.

EXAMPLE 3

Example 3 was executed as example 1, except that 10 grams water, in stead of 0.5 gram water, was charged to the reactor. The resulting TCB content is reported in Table I.

COMPARATIVE EXPERIMENT A

Comparative experiment A was executed as example 1, except that no water was charged to the reactor. The resulting TCB content is reported in Table I.

TABLE I

Experiments and Resulting TCB content and selectivity

| Example/ Comparative experiment | Amount of ACN (grams) | Amount of HCN (grams) | Amount of Water (grams) | Reactor mass | TCB Analysis Wt % | TCB Content (mMol) | TCB Selectivity (%) |
| --- | --- | --- | --- | --- | --- | --- | --- |
| Comparative experiment A | 20 | 9.3 | 0 | 89.3 | 0.22 | 1.48 | 0.43 |
| Example 1 | 20 | 9.3 | 0.5 | 89.8 | 0.175 | 1.18 | 0.34 |
| Example 2 | 20 | 9.3 | 1.0 | 90.3 | 0.095 | 0.65 | 0.19 |
| Example 3 | 20 | 9.3 | 10.0 | 99.3 | 0 | 0 | 0.0 |

The TCB content is calculated as: TCB content (mMol) = (total mass of reactor content) · (weight % TCB) · 10)/(mol. weight TCB) and the TCB selectivity is calculated as: TCB selectivity (%) = TCB content (mMol) · 100/(added HCN (mMol)) · (HCN Conversion) wherein the mol. weight of TCB is 133; added $HCN_{in}$ is 344 mMol and the HCN conversion is 1.

From Table I it is seen that the amount of TCB, formed in the process of preparing succinonitrile from ACN and HCN in the presence of a tertiary amine, is reduced when water is present in the reaction mixture. The results furthermore show that TCB is formed in a lower amount when a larger amount of water is present.

COMPARATIVE EXPERIMENT B

A 150 ml double glass reactor, fitted with a turbine stirrer and baffles and equipped with a reflux cooler, was charged with 80 g succinonitrile and 11 ml (8.0 g) triethylamine. The temperature of the reflux cooler was kept at −9° C. while the reactor content was heated to 70° C. Then 20.0 ml (16.1 g, 300 mMol) ACN and 10.6 ml (7.3 g, 270 mMol) HCN were dosed simultaneously in 30 seconds. After 30 minutes a sample was taken from the reaction mixture. Then the TCB content and HCN content in the reaction mixture were determined with gaschromatography, as a percentage of the total reaction mixture. The resulting TCB content, HCN conversion and TCB selectivity is reported in Table II.

EXAMPLE 4

Example 4 was executed as comparative experiment B, except that in addition to the succinonitrile and the triethylamine, 5 ml (4.0 g) methanol was pre-charged to the reactor. The resulting TCB content, HCN conversion and TCB selectivity is reported in Table II.

EXAMPLE 5

Example 5 was executed as comparative experiment B, except that in addition to the succinonitrile and the triethylamine, 5 ml (3.9 g) ethanol was pre-charged to the reactor. The resulting TCB content, HCN conversion and TCB selectivity is reported in Table II.

EXAMPLE 6

Example 6 was executed as comparative experiment B, except that in addition to the succinonitrile and the triethylamine, 5 ml (4.0 g) t-butanol was pre-charged to the reactor. The resulting TCB content, HCN conversion and TCB selectivity is reported in Table II.

EXAMPLE 7

Example 7 was executed as comparative experiment B, except that in addition to the succinonitrile and the triethylamine, 3,7 ml (3.9 g) phenol was pre-charged to the reactor. The resulting TCB content, HCN conversion and TCB selectivity is reported in Table II.

EXAMPLE 8

Example 8 was executed as comparative experiment B, except that in addition to the succinonitrile and the triethylamine, 4 ml (4.2 g) acetic acid was pre-charged to the reactor. The resulting TCB content, HCN conversion and TCB selectivity is reported in Table II.

TABLE II

Experiments and resulting TCB content and selectivity

| Experiment | Compound | Amount (g) | TCB Analysis (weight. %) | TCB content (mMol) | HCN conversion | TCB Selectivity (%) |
|---|---|---|---|---|---|---|
| Comparative Experiment B | — | — | 0.11 | 0.92 | 0.80 | 0.43 |
| Example 4 | Methanol | 4.0 | 0.05 | 0.43 | 1.0 | 0.16 |
| Example 5 | Ethanol | 3.9 | 0.07 | 0.61 | 0.97 | 0.23 |
| Example 6 | t-butanol | 4.0 | 0.10 | 0.86 | 0.99 | 0.32 |
| Example 7 | Phenol | 3.9 | 0.04 | 0.35 | 1.0 | 0.13 |
| Example 8 | Acetic acid | 4.2 | 0.11 | 0.92 | 1.0 | 0.34 |

The TCB content is calculated as: TCB content (mMol) = (total mass of reactor content) · (weight % TCB) · 10/(mol. weight TCB) and the TCB selectivity is calculated as: TCB selectivity (%) = TCB content (mMol) · 100/(added HCN (mMol)) · (HCN Conversion) wherein the mol. weight of TCB is 133; added $HCN_{in}$ is 270 mMol and the total mass of reactor content is 111 g, without additive, and about 115 g with additive.

From Table II it is seen that the amount of TCB, formed in the process for preparing succinonitrile from ACN and HCN in the presence of a tertiary amine, is reduced when an alcohol or carboxylic acid is present in the reaction mixture. The results furthermore show that the HCN conversion after 30 minutes reaction time is higher when an alcohol or carboxylic acid is present compared with the comparative experiment B, wherein no additional compound chosen from the group consisting of water, aliphatic alcohols, aromatic alcohols, carboxylic acids and mixtures thereof is present.

The invention claimed is:

1. Process for preparing succinonitrile (SN) by contacting acrylonitrile (ACN) with hydrocyanic acid (HCN) as reactants in a reactor in the presence of a tertiary amine, wherein the process is carried out in the presence of a compound chosen from the group consisting of water, aliphatic alcohols, aromatic alcohols, carboxylic acids and mixtures thereof.

2. Process according to claim 1, wherein the compound is chosen from the group consisting of water, aliphatic alcohols and mixtures thereof.

3. Process according to claim 1, wherein the compound is present in an amount of at least 1% by weight, calculated relative to the reactants.

4. Process according to claim 1, wherein the compound contains water.

5. Process according to claim 1, wherein the compound contains an aliphatic alcohol chosen from the group of C1-C12 alcohols.

6. Process according to claim 1, wherein the compound contains phenol or a substituted phenol.

7. Process according to claim 1, wherein the compound contains a carboxylic acid chosen from the group of acetic acid, propionic acid, butyric acid and iso-butyric acid.

8. Process according to claim 1, wherein the tertiary amine is a trialkyl amine.

9. Process according to claim 8, wherein the trialkyl amine is triethylamine.

10. Process according to claim 1, wherein the tertiary amine is present in a concentration of at least 2% by weight, calculated relative to the total of ACN, HCN and/or reaction products thereof, the compound chosen from the group consisting of water, aliphatic alcohols, aromatic alcohols, carboxylic acids and mixtures thereof, the tertiary amine and any non-reactive diluent present in the reactor.

11. Process according to claim 1, wherein ACN and HCN are contacted in a mole ratio of ACN:HCN of at least 1.0:1 up to at most 1.25:1.

12. Process according to claim 1, wherein ACN is present in a concentration of at most 35% by weight, calculated relative to the total of ACN, HCN AND/OR reaction products thereof, the compound chosen from the group consisting of water, aliphatic alcohols, aromatic alcohols, carboxylic acids and mixtures thereof, the tertiary amine and any non-reactive diluent present in the reactor.

13. Process according to claim 1, wherein the process is carried out in the presence of a non-reactive diluent.

14. Process according to claim 13, wherein the non-reactive diluent is succinonitrile.

15. Process according to claim 14, wherein succinonitrile is present in a concentration of at least 40% by weight, calculated relative to the total of ACN, HCN and/or reaction products thereof, the compound chosen from the group consisting of water, aliphatic alcohols, aromatic alcohols, carboxylic acids and mixtures thereof, the tertiary amine and succinonitrile present in the reactor.

16. Process according to wherein the process is conducted at a temperature between 60° C. and 80° C.

* * * * *